(12) United States Patent
Thornton

(10) Patent No.: US 6,464,924 B1
(45) Date of Patent: Oct. 15, 2002

(54) METHOD OF FORMING A CUSTOM MASK USING AN IMPRESSION MASK

(75) Inventor: W. Keith Thornton, 5524 Edlen, Dallas, TX (US) 75220

(73) Assignee: W. Keith Thornton, Dallas, TX (US)

( * ) Notice: Subject to any disclaimer, the term of this patent is extended or adjusted under 35 U.S.C. 154(b) by 0 days.

(21) Appl. No.: 09/543,406

(22) Filed: Apr. 5, 2000

(51) Int. Cl.[7] .......................... A62B 7/00; A61M 16/00; C08J 5/00
(52) U.S. Cl. ............. 264/331.12; 264/222; 264/331.24; 264/331.11; 425/2; 425/816; 128/206.12; 128/206.24
(58) Field of Search .......................... 264/222, 16, 17, 264/18, 19, 20, 319, 221, 330, 331.11, 331.12, 331.24; 425/2, DIG. 11, 815, 816; 604/72; 128/206.16, 206.21, 206.24, 206.28, 207.13, 206.12; 2/173, 206; D24/110.1–110.4

(56) References Cited

U.S. PATENT DOCUMENTS

| | | | |
|---|---|---|---|
| 339,334 A | * | 4/1886 | Searle |
| 690,663 A | | 1/1902 | Pratt |
| 746,869 A | | 12/1903 | Moulton |
| 774,446 A | | 11/1904 | Moulton |
| 885,196 A | | 4/1908 | Steil |
| 893,213 A | | 7/1908 | Whiteway |
| 955,562 A | * | 4/1910 | Thomas |
| 996,783 A | * | 7/1911 | Moreau |
| 1,076,534 A | | 10/1913 | Wallen |
| 1,146,264 A | | 7/1915 | Kelly |
| 1,483,694 A | | 2/1924 | Stukey |
| 1,649,664 A | | 11/1927 | Carter |
| 1,674,336 A | | 6/1928 | King |
| 1,675,202 A | * | 6/1928 | Warne |
| 1,679,748 A | * | 8/1928 | Stratton |
| 2,171,695 A | | 9/1939 | Harper ........................ 32/19 |
| 2,178,128 A | | 10/1939 | Waite ........................ 128/136 |
| 2,383,649 A | | 8/1945 | Heidbrink .................... 128/142 |
| 2,424,533 A | | 7/1947 | Faires ........................ 128/136 |
| 2,505,028 A | | 4/1950 | Boeger ...................... 128/215 |

(List continued on next page.)

FOREIGN PATENT DOCUMENTS

| | | | |
|---|---|---|---|
| AU | 27647/95 | of 1998 | .......... A62B/18/98 |
| AU | 78762/94 | of 1998 | ............ A61F/5/56 |
| DE | 156627 | 12/1904 | |
| EP | 0312368 | 4/1989 | ............ A61F/5/56 |
| EP | 0359135 | 3/1990 | .......... A63B/71/10 |
| GB | 1569129 | 6/1980 | ............ A61F/5/56 |
| GB | 2072567 A | * 10/1981 | |
| WO | WO 91/2777 | 9/1991 | ............ A61C/9/00 |

OTHER PUBLICATIONS

Mayo Clinic Health Letter, vol. 13, No. 7, "Snoring.", Jul. 1995.

Photocopies of 2–piece dental device manufactured by Currie–Gibson Dental Laboratory, Inc. prior to Apr. 13, 1993.

(List continued on next page.)

Primary Examiner—Jan H. Silbaugh
Assistant Examiner—Geoffrey P. Shipsides
(74) Attorney, Agent, or Firm—Baker Botts L.L.P.

(57) ABSTRACT

A method of forming a custom mask (40) includes introducing a deformable material (32) to an impression mask (24) and directing the deformable material (32) against at least a portion of a user's face within the impression mask (24). This forms an impression of the user's face in the deformable material (32) to form the custom mask (40). The impression mask (24) receives the deformable material (32) and directs the deformable material (32) against at least a portion of a user's face within the impression mask (24) in response to pressure applied to the impression mask (24). The deformable material (32) may include a polycaprolactone polymer or an aliphatic polyester. The impression mask (24) may receive the deformable material (32) either before the user's face is brought within the impression mask (24) or while the user's face is within the impression mask (24).

13 Claims, 2 Drawing Sheets

U.S. PATENT DOCUMENTS

| | | | |
|---|---|---|---|
| 2,521,039 A | 9/1950 | Carpenter | 128/136 |
| 2,521,084 A | 9/1950 | Oberto | 128/141 |
| 2,531,222 A | 11/1950 | Kesling | 32/14 |
| 2,547,419 A * | 4/1951 | Sugarman et al. | |
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,671,446 A * | 3/1954 | Mann | |
| 2,712,160 A * | 7/1955 | Sterczak | |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 3,037,501 A | 6/1962 | Miller | 128/141 |
| 3,064,354 A | 11/1962 | Pos | 32/19 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,832 A | 5/1967 | Weisberg | 32/32 |
| 3,360,860 A * | 1/1968 | Roland | |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,658,058 A | 4/1972 | Neidhart et al. | 128/147 |
| 3,690,004 A | 9/1972 | Frush | 32/17 |
| 3,768,465 A * | 10/1973 | Helmer | |
| 3,845,768 A * | 11/1974 | Garrahan | |
| 3,854,208 A | 12/1974 | Arant | 32/19 |
| 3,864,832 A | 2/1975 | Carlson | 128/136 |
| 3,871,370 A | 3/1975 | McDonald | 128/136 |
| 3,882,601 A | 5/1975 | Jahn | 32/17 |
| 3,884,226 A | 5/1975 | Tepper | 128/136 |
| 4,016,650 A | 4/1977 | Leusner et al. | 32/17 |
| 4,026,024 A | 5/1977 | Tradowsky | 32/19 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,233,972 A | 11/1980 | Hauff et al. | 128/205 |
| 4,289,127 A | 9/1981 | Nelson | 128/207.14 |
| 4,304,227 A | 12/1981 | Samelson | 128/136 |
| 4,345,592 A | 8/1982 | Giorgini et al. | 128/204 |
| 4,345,593 A | 8/1982 | Sullivan | 128/204 |
| 4,376,628 A | 3/1983 | Aardse | 433/80 |
| 4,382,783 A | 5/1983 | Rosenberg | 433/19 |
| 4,392,490 A | 7/1983 | Mattingly et al. | 128/202 |
| 4,397,701 A * | 8/1983 | Johnson et al. | |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,454,090 A * | 6/1984 | Saumell | |
| 4,470,413 A | 9/1984 | Warncke | 128/201.18 |
| 4,495,945 A | 1/1985 | Liegner | 128/200.26 |
| 4,505,672 A | 3/1985 | Kurz | 433/6 |
| 4,530,662 A | 7/1985 | Andersson et al. | 433/37 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,668,188 A | 5/1987 | Wolfenson et al. | 433/37 |
| 4,669,459 A | 6/1987 | Spiewak et al. | 128/136 |
| 4,676,240 A | 6/1987 | Gardy | 128/207.14 |
| 4,706,683 A | 11/1987 | Chilton et al. | 128/654 |
| 4,715,368 A | 12/1987 | George | 128/136 |
| 4,773,853 A | 9/1988 | Kussick | 433/6 |
| 4,784,123 A | 11/1988 | Robeson | 128/90 |
| 4,799,500 A | 1/1989 | Newbury | 128/859 |
| 4,858,606 A | 8/1989 | Hamlin | 128/204 |
| 4,862,903 A | 9/1989 | Campbell | 128/861 |
| 4,870,962 A | 10/1989 | Sitnik | 128/205 |
| 4,886,056 A | 12/1989 | Simpson | 128/201 |
| 4,892,478 A | 1/1990 | Tateosian et al. | 433/6 |
| 4,901,737 A | 2/1990 | Toone | 128/848 |
| 4,906,234 A | 3/1990 | Voychehovski | 604/79 |
| 4,919,128 A | 4/1990 | Kopala et al. | 128/207.18 |
| 4,932,867 A | 6/1990 | Ueno | 433/69 |
| 4,941,212 A * | 7/1990 | Liff | |
| 4,955,393 A | 9/1990 | Adell | 128/859 |
| 4,957,124 A * | 9/1990 | Mooney | |
| RE33,442 E | 11/1990 | George | 128/860 |
| 5,003,994 A | 4/1991 | Cook | 128/848 |
| 5,011,407 A | 4/1991 | Pelerin | 433/48 |
| 5,018,533 A | 5/1991 | Hawkins | 128/848 |
| 5,026,278 A | 6/1991 | Oxman et al. | 433/41 |
| 5,028,232 A | 7/1991 | Snow | 433/24 |
| 5,040,976 A | 8/1991 | Ubel, III et al. | 433/41 |
| 5,042,478 A | 8/1991 | Kopala et al. | 128/207.18 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,055,039 A | 10/1991 | Abbatte et al. | 433/24 |
| 5,056,534 A | 10/1991 | Wright | 128/848 |
| 5,064,371 A | 11/1991 | Smeltzer | 433/37 |
| 5,065,756 A | 11/1991 | Rapoport | 128/204 |
| 5,066,231 A | 11/1991 | Oxman et al. | 433/214 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,112,225 A | 5/1992 | Diesso | 433/48 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,190,457 A | 3/1993 | Schreinemakers | 433/214 |
| 5,193,532 A | 3/1993 | Moa et al. | 128/204 |
| 5,213,498 A | 5/1993 | Pelerin | 433/37 |
| 5,243,971 A | 9/1993 | Sullivan et al. | 128/205 |
| 5,245,995 A | 9/1993 | Sullivan et al. | 128/204 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,320,533 A | 6/1994 | Lee | 433/218 |
| 5,365,945 A | 11/1994 | Halstrom | 128/848 |
| 5,370,533 A | 12/1994 | Bushnell | 433/36 |
| 5,373,859 A | 12/1994 | Forney | 128/846 |
| 5,409,017 A | 4/1995 | Lowe | 128/848 |
| 5,415,544 A | 5/1995 | Oxman et al. | 433/48 |
| 5,427,117 A | 6/1995 | Thornton | 128/848 |
| 5,456,264 A | 10/1995 | Series et al. | 128/725 |
| 5,458,137 A | 10/1995 | Axe et al. | 128/204 |
| 5,477,850 A | 12/1995 | Zegler et al. | 128/202 |
| 5,503,146 A | 4/1996 | Froehlich et al. | 128/204 |
| 5,503,552 A | 4/1996 | Diesso | 433/37 |
| 5,517,983 A | 5/1996 | Deighan et al. | 128/204 |
| 5,537,994 A | 7/1996 | Thornton | 128/205 |
| 5,537,999 A | 7/1996 | Dearman et al. | 128/205 |
| 5,538,000 A | 7/1996 | Rudolph | 128/205 |
| 5,551,419 A | 9/1996 | Froehlich et al. | 128/204 |
| 5,551,872 A | 9/1996 | Mena | 433/37 |
| 5,558,090 A | 9/1996 | James | 128/207.18 |
| RE35,339 E | 10/1996 | Rapoport | 128/204 |
| 5,560,354 A | 10/1996 | Berthon-Jones et al. | 128/205 |

| | | |
|---|---|---|
| 5,562,449 A | 10/1996 | Jacobs et al. .................. 433/215 |
| 5,566,683 A | 10/1996 | Thornton ..................... 128/848 |
| 5,582,517 A | 12/1996 | Adell ............................... 433/6 |
| 5,592,935 A | 1/1997 | Elstran et al. ............... 128/205 |
| 5,611,485 A | 3/1997 | Davis ............................. 239/8 |
| 5,657,751 A | 8/1997 | Karr, Jr. ....................... 128/205 |
| 5,657,752 A | 8/1997 | Landis et al. ................ 128/207 |
| 5,676,133 A | 10/1997 | Hickle et al. ................ 128/205 |
| 5,678,567 A | 10/1997 | Thornton et al. ............ 128/848 |
| 5,687,715 A | 11/1997 | Landis et al. ........... 128/207.18 |
| 5,713,349 A | 2/1998 | Keaney ....................... 128/204 |
| 5,718,244 A | 2/1998 | Thornton ..................... 128/864 |
| 5,718,500 A | 2/1998 | Vinci guerra et al. ........... 2/431 |
| 5,720,280 A | 2/1998 | Elstran et al. ............... 128/205 |
| 5,720,302 A | 2/1998 | Belfer .................... 128/201.26 |
| 5,746,201 A | 5/1998 | Kidd ........................... 128/206 |
| 5,752,510 A | 5/1998 | Goldstein .................... 128/207 |
| 5,755,219 A | 5/1998 | Thornton ..................... 128/201 |
| 5,807,100 A | 9/1998 | Thornton ....................... 433/48 |
| 5,829,441 A | 11/1998 | Kidd et al. ................... 128/848 |
| 5,832,918 A * | 11/1998 | Pantino |
| 5,846,082 A | 12/1998 | Thornton ..................... 433/215 |
| 5,887,587 A | 3/1999 | Groenke ...................... 128/207 |
| 5,891,372 A * | 4/1999 | Besset et al. |
| 5,954,048 A | 9/1999 | Thornton ..................... 128/201 |
| 5,983,892 A | 11/1999 | Thornton ..................... 128/201 |
| 5,988,166 A | 11/1999 | Hayek ......................... 128/205 |
| 6,012,455 A | 1/2000 | Goldstein .................... 128/207 |
| 6,109,265 A | 8/2000 | Frantz et al. ................ 128/848 |
| 6,318,997 B1 * | 11/2001 | Mayweather |

OTHER PUBLICATIONS

Farrar & McCarty, "A Clinical Outline of Temporomandibular Joint Diagnosis and Treatment," Normandie Study Group for TMJ Dysfunction, 3 pages, 1983.
Professional Positioners brochure, "Dedicated to Excellence," 4 pages, Unknown.
Great Lakes Orthodontics, Ltd., "Nocturnal Airway Patency Appliance™ (NAPA)," General Instructions, 2 pages.
Schmidt–Nowara, et al., "Oral Appliances for the Treatment of Snoring and Obstructive Sleep Apnea: A Review," Sleep, 18(6):501–510, 1995.
George, "Treatment of Snoring and Obstructive Sleep Apnea with a Dental Device," General Dentistry, 5 pages, Jul.–Aug. 1993.
Database WOI, Section PQ, Week 9039, Derwent Publications, Ltd., London, GB XP–002116355—Abstract "Surgical Mouth Air Duct." Dec. 15, 1989.
CPAP/PRO®. . . Introducing a New Comfort Level for CPAP Users!! brochure (2 pages). No date.
W. Keith Thornton, "Combination Face Mask and Dental Device for Improved Breathing During Sleep," USSN 08/594,904 filed Jan. 31, 1996 (019651.0129).
W. Keith Thornton, "Method and Apparatus for Adjusting a Dental Device," U.S. appln. Ser. No. 08/787,529, pending (019651.0152), Jun. 15, 1999.
W. Keith Thornton, "Apparatus for Prevention of Snoring and Improved Breathing During Sleep," U.S. appln. Ser. No. 08/828,523, pending (019651.0154), Mar. 31, 1997.
W. Keith Thornton, "Method and Apparatus for Adjusting a Dental Device," U.S. appln. Ser. No. 08/787,529, pending (019651.0166), Jan. 21, 1997.
W. Keith Thornton, "Device for Improving Breathing," U.S. appln. Ser. No. 09/290,512, pending (019651.0174), Jan. 31, 1996.
W. Keith Thornton, "Device for Improving Breathing and Method for Fitting Same," U.S. appln. Ser. No. 09/396,986, pending (019651.0175), Sep. 15, 1999.
W. Keith Thornton, "Oral Appliance Having a Bonding Layer and Method for Fitting and Relining Same," USSN 09/483,741 (019651.0178), Jul. 17, 2000.
PCT International Search Report, PCT/US97/08708, 4 pages, Aug. 12, 1997.
W. Keith Thornton and Andrew O. Jamieson, "Method and Apparatus for Adjusting a Dental Device," U.S. appln. Ser. No. 08/218,719, abandoned (019651.0105), Mar. 24, 1994.
W. Keith Thornton, "Apparatus for Prevention of Snoring and Improved Breathing During Sleep," U.S. appln. Ser. No. 08/363,639, abandoned (019651.0112), Dec. 24, 1994.
W. Keith Thornton and Andrew O. Jamieson, "Method and Apparatus for Adjusting a Dental Device," U.S. appln. Ser. No. 08/435,277, abandoned (019651.0119), May 5, 1995.
W. Keith Thornton, "Device for Improving Breathing," U.S. appln. Ser. No. 08/582,526, abandoned (019651.0121), Jan. 3, 1996.

* cited by examiner

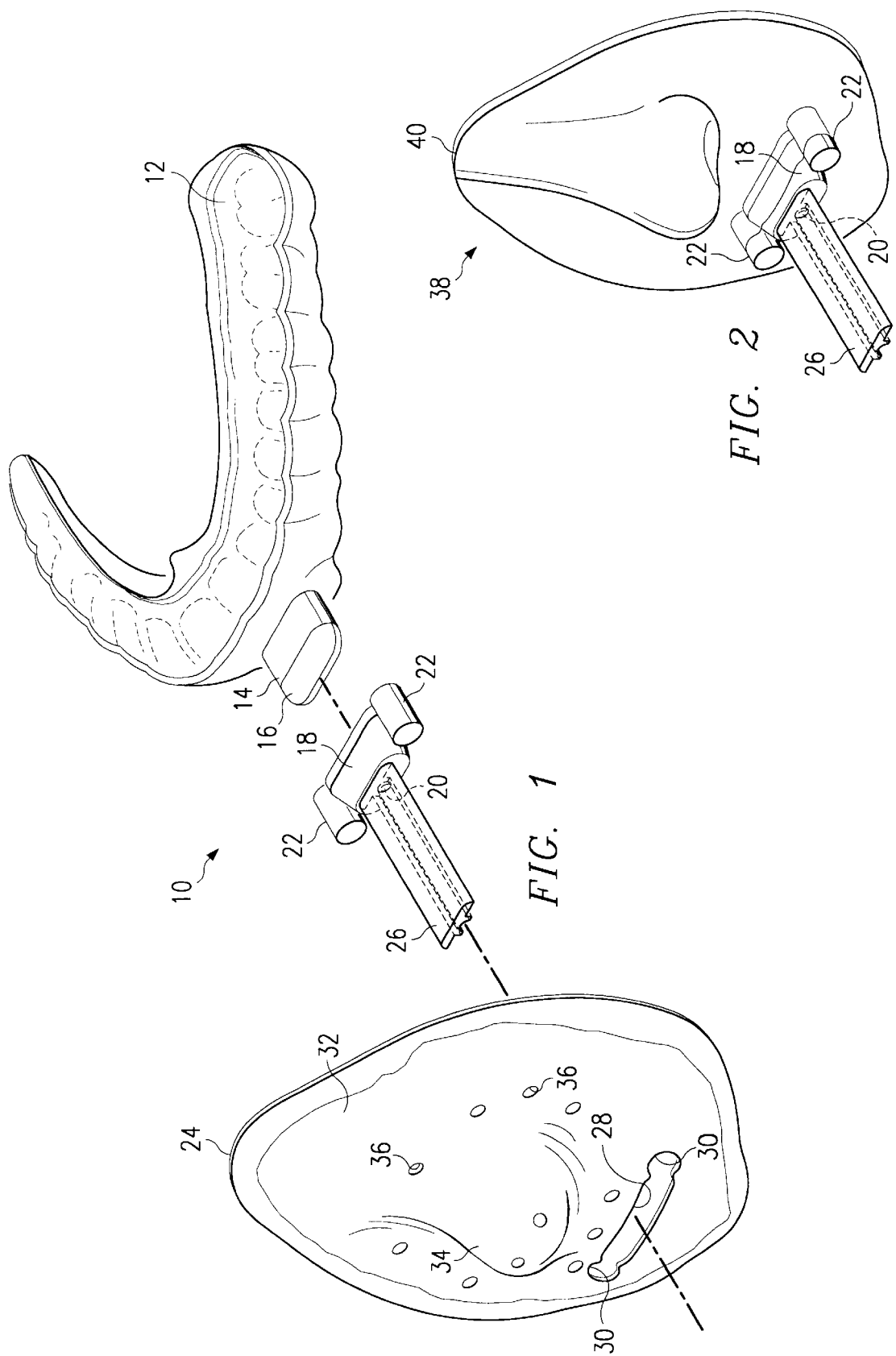

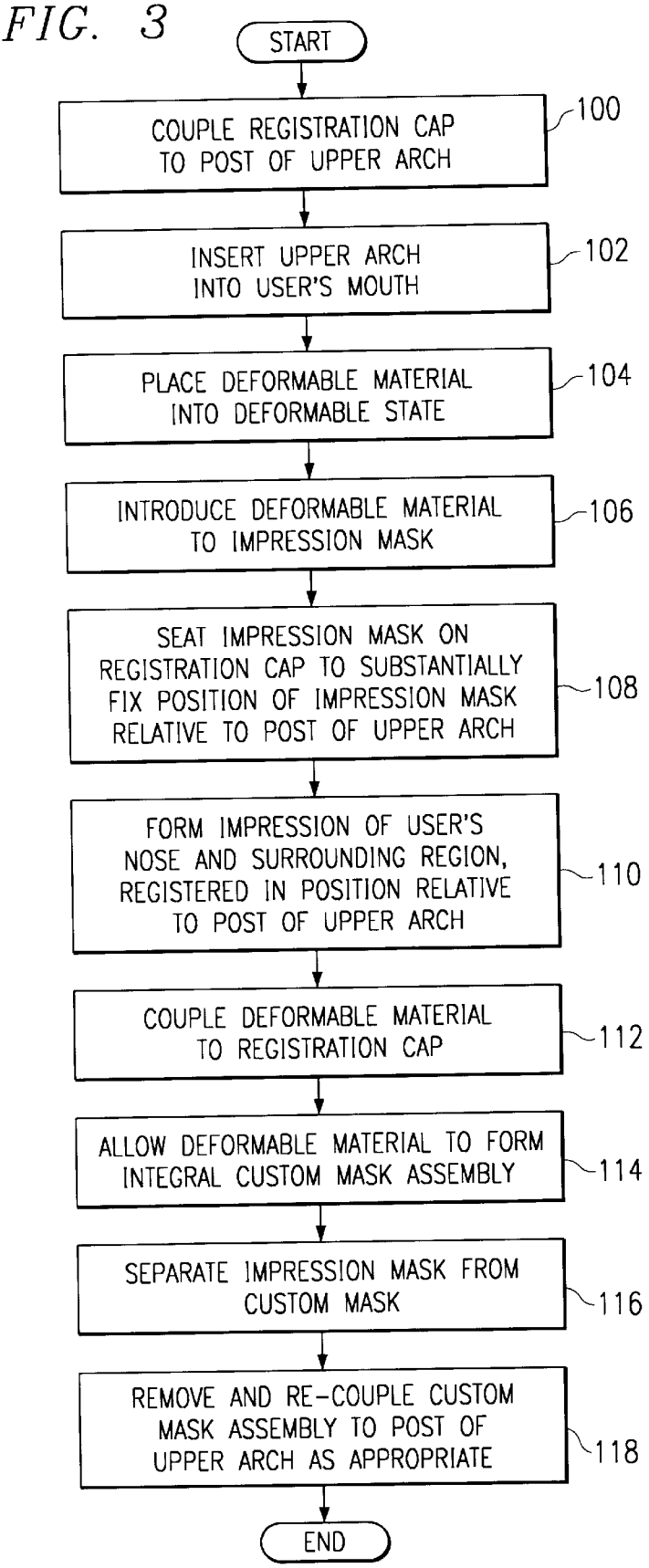

METHOD OF FORMING A CUSTOM MASK USING AN IMPRESSION MASK

CROSS REFERENCE TO RELATED APPLICATIONS

This application is related to U.S. application Ser. No. 09/543,405 entitled "Oral Appliance for Improving Breathing and Method of Constructing Same," U.S. application Ser. No. 09/543,397 entitled "Custom Mask and Method of Forming Same," U.S. application Ser. No. 09/543,398 entitled "Custom Mask Assembly and Method for Making Same," and U.S. application Ser. No. 09/543,402 entitled "Device for Improving Breathing and Method of Constructing Same," all filed Apr. 5, 2000 by W. Keith Thornton.

This application is also related to U.S. application Ser. No. 08/594,904, filed Jan. 31, 1996, by W. Keith Thornton and entitled "Device for Improving Breathing," which is a continuation of U.S. application Ser. No. 08/253,949, filed Jun. 3, 1994, by W. Keith Thornton and entitled "Combination Face Mask and Dental Device for Improved Breathing During Sleep" (now U.S. Pat. No. 5,537,994).

This application is also related to U.S. application Ser. No. 08/828,523, filed Mar. 31, 1997, by W. Keith Thornton and entitled "Apparatus for Prevention of Snoring and Improved Breathing During Sleep," which is a file wrapper continuation of U.S. application Ser. No. 08/363,639, filed Dec. 24, 1994, by W. Keith Thornton and entitled "Apparatus for Prevention of Snoring and Improved Breathing During Sleep" (now abandoned), which is a continuation of U.S. application Ser. No. 08/129,598, filed Sep. 29, 1993, by W. Keith Thornton and entitled "Apparatus for Prevention of Snoring and Improved Breathing During Sleep" (now U.S. Pat. No. 5,427,117).

This application is also related to U.S. application Ser. No. 08/787,529, filed Jan. 21, 1997, by W. Keith Thornton and entitled "Method and Apparatus for Adjusting a Dental Device," which is a file wrapper continuation of U.S. application Ser. No. 08/435,277, filed May 5, 1995, by W. Keith Thornton and Andrew O. Jamieson and entitled "Method and Apparatus for Adjusting a Dental Device" (now abandoned), which is a file wrapper continuation of U.S. application Ser. No. 08/218,719, filed Mar. 24, 1994, by W. Keith Thornton and Andrew O. Jamieson and entitled "Method and Apparatus for Adjusting a Dental Device" (now abandoned).

This application is also related to U.S. application Ser. No. 09/333,874, filed Jun. 15, 1999, by W. Keith Thornton and entitled "Device and Method for Improving Breathing and Method for Fitting Same," which is based on U.S. Provisional Application No. 60/089,628, filed Jun. 16, 1998.

This application is also related to U.S. application Ser. No. 09/290,512, filed Apr. 12, 1999, by W. Keith Thornton and entitled "Device for Improving Breathing," which is a continuation of U.S. application Ser. No. 08/878,998, filed Jun. 19, 1997, by W. Keith Thornton and entitled "Device for Improving Breathing" (now U.S. Pat. No. 5,983,892), which is a continuation of U.S. application Ser. No. 08/582,526, filed Jan. 3, 1996 by W. Keith Thornton and entitled "Device for Improving Breathing" (now abandoned), which is a continuation-in-part of U.S. application Ser. No. 08/253,949.

This application is also related to U.S. application Ser. No. 09/396,986, filed Sep. 15, 1999 by W. Keith Thornton and entitled "Device for Improving Breathing and Method of Fitting Same."

This application is also related to U.S. application Ser. No. 09/483,741, filed Jan. 17, 2000 by W. Keith Thornton and entitled "Oral Appliance Having a Bonding Layer and Methods for Fitting and Relining Same."

This application is also related to U.S. application Ser. No. 09/554,771, filed May 16, 2000 by W. Keith Thornton and entitled "Device and Method for Improving Breathing."

TECHNICAL FIELD OF THE INVENTION

This invention relates generally to the field of face masks, and more particularly to a custom mask formed using an impression mask.

BACKGROUND OF THE INVENTION

Many people experience breathing problems on a recurring basis, which often results in difficulty sleeping, in snoring, or in other more serious conditions such as obstructive sleep apnea. One treatment for such breathing problems involves use of a device inserted into a user's mouth for extending the user's lower jaw forward. These devices help to open the user's breathing passage more fully to allow easier breathing through the user's nose and mouth.

As technology advances and people with breathing problems demand increased performance and comfort, improving the breathing of the users becomes increasingly important. Previous devices for improving breathing include custom masks connected to an associated oral appliance. Such an oral appliance may extend the user's lower jaw forward to open the breathing passage, while the mask allows air or another gas to be delivered to the user's nose at positive pressure to further open the breathing passage. Previous masks are often relatively expensive due to the expertise that is often required to design and manufacture the masks and fit them to the users. Furthermore, previous masks have often been fitted to the user's particular bone structure and facial features poorly, if at all. As a result, previous masks have failed to adequately prevent venting from around the perimeter of the mask, have caused discomfort for the users, and have been ineffective in treating breathing problems such as snoring and sleep apnea. As a result of these and other deficiencies, previous masks are inadequate for the needs of many users who experience breathing difficulties.

SUMMARY OF THE INVENTION

According to the present invention, problems and disadvantages associated with previous custom masks and methods for making them have been substantially reduced or eliminated.

According one embodiment of the present invention, a method of forming a custom mask includes introducing a deformable material to an impression mask and directing the deformable material against at least a portion of a user's face within the impression mask. This forms a resulting impression of the user's face in the deformable material to form the custom mask. In a more particular embodiment, the deformable material includes a polycaprolactone polymer or an aliphatic polyester. In another more particular embodiment, the deformable material is introduced to the impression mask before the user's face is brought within the impression mask.

According to another embodiment of the present invention, an impression mask for forming a custom mask receives a deformable material and directs the deformable material against at least a portion of a user's face within the impression mask in response to pressure applied to the impression mask. The impression mask forms a mold of at least the portion of the user's face in the deformable material to form the custom mask. In a more particular embodiment, the deformable material includes a polycaprolactone polymer or an aliphatic polyester. In another embodiment, the impression mask may receive the deformable material before the user's face is brought within the impression mask or while the user's face is within the impression mask.

The custom mask and method of making it according to the present invention provide important technical advantages. In contrast to prior techniques, the impression mask of the present invention allows the custom mask to be made and fitted to a user relatively quickly and easily, with little expertise required, typically resulting in better efficiency for clinical professionals and reduced cost to users. In contrast to previous masks, the custom mask of the present invention is fitted substantially optimally to the particular user's facial structure and features. As a result, the custom mask provides improved fit, reduced venting, increased comfort, and better performance, whether in treating breathing problems such as snoring and sleep apnea or for any other suitable purpose for which the custom mask is used. Other technical advantages will be readily apparent to those skilled in the art.

BRIEF DESCRIPTION OF THE DRAWINGS

For a more complete understanding of the present invention and its advantages, reference is now made to the following descriptions taken in conjunction with the accompanying drawings, in which like reference numbers indicate like features and wherein:

FIG. 1 illustrates an exemplary impression mask being registered in position relative to an associated oral appliance;

FIG. 2 illustrates an exemplary custom mask assembly; and

FIG. 3 is a flow chart illustrating an exemplary method of making a custom mask assembly that is registered in position relative to an associated oral appliance.

DETAILED DESCRIPTION OF THE INVENTION

FIG. 1 illustrates an exemplary system 10 for constructing a face, nose, or other mask that is registered relative to an associated custom, non-custom, or other oral appliance. In one embodiment, the oral appliance includes at least an upper arch 12. A lower arch (not explicitly shown) may be coupled to upper arch 12 in any appropriate manner and for any suitable purpose. For example only and not by way of limitation, upper arch 12 may be coupled to a lower arch using a suitable deformable material as described in co-pending U.S. Application No. 09/543,405, filed on Apr. 5, 2000 for a "Device for Improving Breathing and Method of Constructing Same," may be coupled to a lower arch using a suitable hooking mechanism as described in U.S. Pat. No. 5,954,048, or may be coupled to a lower arch in any other appropriate manner. In one embodiment, a lower arch may be coupled to upper 12 so that the lower arch may be secured in a fixed forward position relative to upper arch 12 to extend the user's lower jaw forward. This opens the user's breathing passage and helps to reduce or eliminate breathing problems such as snoring and sleep apnea.

An outwardly extending post 14 is coupled to or integrally formed with upper arch 12 and includes a tapered portion 16 for force fitting post 14 into hollow 36 of registration cap 18. Although tapered portion 16 of post 14 is shown as being rounded to some extent, the present invention contemplates tapered portion 16 being angled or having another shape appropriate to cooperate with the internal shape of hollow 36 in registration cap 18. The present invention further contemplates a latch, knob or other protrusion, or another suitable mechanism to help secure registration cap 18 to tapered portion 16 to. Instead of or in addition to the above, a screw or other suitable fastener 20 may permanently or removably couple registration cap 18 to post 14. The tapered portion 16 may be integral to the remainder of post 14, may be screwed or otherwise coupled to the remainder of post 14, may rotate relative to the remainder of post 14 to adjust the forward position of an associated lower arch (as described in U.S. Pat. No. 5,954,048, for example), or may have any other suitable relationship to the remainder of post 14.

In one embodiment, registration cap 18 includes one or more spacers 22 used for registering the position of registration cap 18, and thus the position of upper arch 12, relative to an impression mask 24. Providing accurate registration between impression mask 24 and upper arch 12 allows a custom mask to be formed using impression mask 24 such that the custom mask and upper arch 12 will be properly horizontally spaced, vertically spaced, rotated, and otherwise configured relative to one another to properly fit the particular user's bone structure and facial features. With previous custom masks, proper fit has been the primary obstacle to achieving reduced venting from around the mask perimeter, sufficient comfort for the user, and other treatment goals. The present invention overcomes these obstacles, providing an important technical advantage over previous mask construction techniques. As shown, registration cap 18 may include an extended arm 26 for coupling the upper arch 12 to one or more other components for improving the user's breathing, as described more fully in co-pending U.S. application Ser. No. 09/543,402 filed Apr. 5, 2000 for a "Device for Improving Breathing and Method of Constructing Same."

Impression mask 24 includes an opening 28 shaped to cooperate with the shape of registration cap 18 and spacers 22. In a particular embodiment, the spacers 22 are substantially cylindrical and opening 28 of face shield 26 includes cooperating rounded contours 30 to receive spacers 22. However, the present invention contemplates one or more spacers 22 having any appropriate shape, and opening 28 having any appropriate cooperating shape, according to particular needs. Opening 28 of impression mask 24 may seat on registration cap 18 and spacers 22 relatively loosely, relatively tightly, or in any other suitable manner. Although spacers 22 are described, the present invention contemplates registration cap 18 without spacers 22, in which case opening 28 may be shaped to seat impression mask 24 onto registration cap 18 alone. Impression mask 24 may be formed from an acrylic or other suitable material.

Before, during, or after impression mask 24 is seated onto registration cap 18, a deformable material 32 is heated or otherwise placed in a deformable state and placed within impression mask 24 so as to cover appropriate portions of the user's face when deformable material 32 is brought into contact with the user's face. The deformable material 32 may be placed in its deformable state before or after being placed within impression mask 24. In one embodiment, deformable material 32 covers and takes an impression of at least a portion of the user's nose and surrounding regions to produce, once deformable material 32 cools and hardens, a custom nose mask appropriate for delivering air or another suitable gas to the user's nose from a continuous positive air pressure (CPAP) system or other external source. Impression mask 24 may include a deeper concave portion 34 to receive the user's nose, and preferably includes suitable holes 36 to allow excess deformable material 32 to escape as an impression is taken. Deformable material 32 may couple with at least portions of registration cap 18, spacers 22, or both registration cap 18 and the spacers 22 to form an integral assembly incorporating at least the custom mask and registration cap 18. In one embodiment, deformable material 32 may substantially surround registration cap 18 and spacers 22, for increased stability or otherwise.

A suitable deformable material 32 may include, for example only and without limitation, methylmethacrylate, the polycarbonate resin thermoplastic such as that sold as LEXAN, the ethylene-vinyl acetate copolymer resin sold under the name ELVAX, a thermoplastic polymer such as polycaprolactone, or other suitable deformable material. These materials are known in substantially different contexts to those skilled in the art and other suitable materials may be used without departing from the intended scope of the present invention. In a particular embodiment, deformable material 32 includes one or more of the polycaprolactone polymers or other aliphatic polyesters as described in U.S. Pat. Nos. 5,112,225 and 4,784,123, and also in product literature distributed by UNION CARBIDE CORPORATION. One or more polycaprolactone polymers may have the formula:

(1)

where R is an aliphatic hydrocarbon and n may range between approximately 300 to approximately 650. Polycaprolactone polymers display desirable dimensional stability and thermoplasticity during cooling, biocompatibility, and other characteristics making them suitable for uses described herein. However, the present invention contemplates any suitable polycaprolactone polymer, possibly including one or more polycaprolactone polymers with other suitable formulas.

In a particular embodiment, deformable material 32 includes one or more of the TONE P-700, TONE P-767, or TONE P-787 polycaprolactone polymers manufactured by UNION CARBIDE CORPORATION, singly or in any combination. In a more particular embodiment, deformable material 32 may include approximately thirty parts by volume of TONE P-700 and sixty parts by volume of TONE P-767, together with approximately ten parts by volume of one or more other polymers, depending upon the application and particular needs. A light cured material, another polymer, or any other suitable material, such as a filler, coloring agent, stabilizer, antioxidant, or antimicrobial agent, may be used to replace or combine with a polycaprolactone polymer in forming deformable material 32 having any appropriate characteristics, properties, or uses. The present invention contemplates deformable material 32 including any suitable mixture or other combination of polycaprolactone polymers, other polymers, and other suitable materials, compounds, or compositions.

The TONE set of polycaprolactone polymers are described in U.S. Pat. Nos. 5,112,225 and 4,784,123, and in product literature distributed by UNION CARBIDE CORPORATION, as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

$$HO-R-OH \qquad (2)$$

where R is an aliphatic hydrocarbon.

Deformable material 32 may begin as extruded pellets, beads, or rods of uniform, similar, or differing size, or in other suitable form. Deformable material 32 is heated in a microwave oven, in water or other non-solvent neutral liquid, or in any other suitable manner to between approximately 140° F. and approximately 180° F. to place deformable material 32 in its deformable state. Deformable material 32 may be maintained in this deformable state until the pellets, beads, or rods congeal, coalesce, or otherwise combine to form a deformable mass capable of assuming shape and configuration desired. The deformable material 32 may be placed in its deformable state before, during, or after deformable material 32 is introduced to impression mask 24. Deformable material 16 mixes, bonds, reacts, combines, or otherwise couples with the material used to form registration cap 18 while deformable material 32 is in a liquid or other deformable state. In one embodiment, deformable material 32 chemically bonds to registration cap 18, to spacers 22, or to both registration cap 18 and spacers 22 to produce an integral piece incorporating a custom mask and registration cap 18. This assembly may be coupled permanently to the associated oral appliance or alternately removed and re-coupled in accordance with particular needs.

In one embodiment, the upper arch 12 is inserted into the user's mouth and the registration cap 18 is coupled to the tapered portion 16 of post 14 in a suitable manner. Deformable material 32 is applied to impression mask 24, opening 28 of impression mask 24 is properly seated on registration cap 18 and spacers 22, and impression mask 24 is pressed or otherwise brought in contact with a suitable portion of the user's face. Impression mask 24 is adjusted, if necessary, to the proper or other appropriate position relative to upper arch 12. Deformable material 32 mixes, bonds, reacts, combines, or otherwise couples to the registration cap 18 and spacers 22 while it is in a deformable state. Deformable material 32 is then allowed to cool and harden to produce a custom mask that is in a fixed position relative to upper arch 12. Alternatively, deformable material 32 may be introduced into impression mask 24 after impression mask 24 has been seated on registration cap 18. The same or a different deformable material 32 may be used, after formation of the custom mask, to couple the custom mask to registration cap 18. Deformable material 32 may be delivered while in a liquid, melted, or other deformable state using a syringe, hypodermic needle, hot glue gun, or other delivery device or technique.

Impression mask 24 may remain in contact with the user's face or be removed before, during, or after the deformable material 32 fully cools and hardens. Deformable material 32 may be used to form a custom mask in the user's home, in the office of a dental, medical, or other clinical professional, or in any other suitable location. While a particular technique is described, the present invention contemplates any appropriate technique for constructing a custom mask that is accurately registered relative to the position of an associated oral appliance.

FIG. 2 illustrates an exemplary custom mask assembly 38, which includes custom mask 40, constructed according to the present invention. As discussed above, custom mask assembly 38 provides important advantages over previous custom masks such as reduced venting, increased comfort, and other benefits. Although custom mask 40 is described primarily as being formed in connection with an oral appliance and the registration of its position relative to the oral appliance, impression mask 24 may be advantageously used to form custom mask 40 with or without an oral appliance or the registration of its position relative to the oral appliance. Furthermore, although custom mask 40 is described primarily for use in improving a user's breathing in combination with a CPAP system, the present invention contemplates custom mask 40 having any appropriate use or uses, according to particular needs.

FIG. 3 is a flow chart illustrating an exemplary method of constructing a custom mask registered in position relative to an associated oral appliance. The method begins at step 100, where the user or a clinical professional couples registration cap 18 to post 14 of upper arch 12. At step 102, upper arch 12 is inserted into the user's mouth to substantially fix the position of registration cap 18 relative to post 14 and thus the user's upper jaw. The present invention contemplates registration cap 18 being coupled to upper arch 12 before or after upper arch 12 is inserted into the user's mouth. At step 104, deformable material 32 is heated or otherwise placed into a deformable state and, at step 106, deformable material is introduced to impression mask 24. In a particular embodiment, deformable material 32 is placed in the impression mask 24 such that deformable material 32 will substantially surround at least a portion of the user's nose including the nostrils and will also surround or otherwise couple to registration cap 18, spacers 22, or both registration cap 18 and spacers 22.

Impression mask 24 is seated on registration cap 18 at step 108 to substantially fix the position of impression mask 24 relative to post 14 and thus the user's upper jaw. At step 110, the impression mask 24 is pressed against or otherwise brought in contact with the user's face to form a suitable impression of the user's nose and appropriate surrounding regions, registered in position relative to post 14 and thus the user's upper jaw. As described above, excess deformable material 32 may escape through holes 36 in impression mask 24. Deformable material 32 may instead be placed in impression mask 24 after impression mask 24 has been properly seated on the registration cap 18. Deformable material 32 couples to registration cap 18, spacers 22, or both registration cap 18 and spacers 22 at step 112.

At step 114, deformable material 32 is permitted to cool and harden, while in contact with the user's face or after removal from the user's face, to produce an integral custom mask assembly 38. At step 116, custom mask assembly 38, incorporating both the custom mask and registration cap 18, is separated from impression mask 24 and custom mask assembly 38 is ready for use in treating snoring, sleep apnea, or any other appropriate breathing problem. As described above, custom mask assembly 38 may be integral to or separate from upper arch 12. At step 118, assuming assembly 38 is not permanently coupled to upper arch 12, assembly 38 may be repeatedly separated from and re-coupled to upper arch 12 as often as necessary or desirable to improve the user's breathing, according to particular needs.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A method of forming a custom mask operable to be worn on a user's face to facilitate treatment of sleep disordered breathing, comprising:

introducing a deformable material to an impression mask;

directing the deformable material against at least a portion of a user's face within the impression mask, the at least a portion of the user's face comprising a region substantially surrounding the user's nostrils;

forming an impression of the at least a portion of the user's face in the deformable material to form the custom mask, the custom mask operable to be worn on the user's face to facilitate treatment of sleep disordered breathing.

2. The method of claim 1, further comprising allowing excess deformable material to escape through one or more holes in the impression mask.

3. The method of claim 1, wherein the deformable material comprises a polycaprolactone polymer.

4. The method of claim 1, wherein the deformable material comprises an aliphatic polyester.

5. The method of claim 4, wherein the aliphatic polyester has the formula:

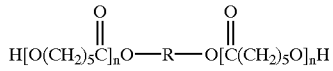

wherein R is an aliphatic hydrocarbon.

6. The method of claim 4, wherein the aliphatic polyester comprises a homopolymer of caprolactone initiated with a diol.

7. The method of claim 1, wherein the deformable material is introduced to the impression mask before the user's face is brought within the impression mask.

8. The method of claim 1, wherein the deformable material comprises a second polymer.

9. A method of forming a custom mask operable to be used to improve a user's breathing, comprising:

introducing a deformable material comprising a polycaprolactone polymer to an impression mask;

directing the deformable material against at least a portion of a user's face within the impression mask;

allowing excess deformable material to escape through one or more holes in the impression mask;

forming an impression of at least a portion of the user's face in the deformable material to form the custom mask operable to be used to improve a user's breathing, the at least a portion of the user's face including a region substantially surrounding the nostrils of the user; and separating the impression mask from the custom mask.

10. The method of claim 9, wherein the polycaprolactone polymer has the formula:

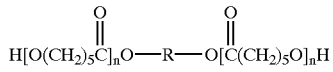

wherein R is an aliphatic hydrocarbon.

11. The method of claim 9, wherein the polycaprolactone polymer is an aliphatic polyester comprising a homopolymer of caprolactone initiated with a diol.

12. The method of claim 9, wherein the deformable material is introduced to the impression mask before the user's face is brought within the impression mask.

13. The method of claim 9, wherein the deformable material comprises a second polymer.

* * * * *